United States Patent
Connolly et al.

(10) Patent No.: US 9,968,643 B2
(45) Date of Patent: May 15, 2018

(54) SELECTION AND USE OF LACTIC ACID BACTERIA PREVENTING BONE LOSS IN MAMMALS

(71) Applicants: BIOGAIA AB, Stockholm (SE); Michigan State University, East Lansing, MI (US)

(72) Inventors: Eamonn Connolly, Lidingö (SE); Robert Allen Britton, East Lansing, MI (US); Laura Rae McCabe, Haslett, MI (US)

(73) Assignees: BIOGAIA AB, Stockholm (SE); MICHIGAN STATE UNIVERSITY, East Lansing, MI (US)

( * ) Notice: Subject to any disclaimer, the term of this patent is extended or adjusted under 35 U.S.C. 154(b) by 0 days. days.

(21) Appl. No.: 15/331,346

(22) Filed: Oct. 21, 2016

(65) Prior Publication Data
US 2017/0128501 A1 May 11, 2017

Related U.S. Application Data

(62) Division of application No. 14/405,496, filed as application No. PCT/SE2013/050646 on Jun. 4, 2013, now abandoned.

(60) Provisional application No. 61/689,338, filed on Jun. 4, 2012.

(51) Int. Cl.
| | |
|---|---|
| *A61K 35/747* | (2015.01) |
| *C12N 1/20* | (2006.01) |
| *C12Q 1/68* | (2006.01) |
| *A23L 33/135* | (2016.01) |
| *A61K 35/00* | (2006.01) |

(52) U.S. Cl.
CPC .......... *A61K 35/747* (2013.01); *A23L 33/135* (2016.08); *C12N 1/20* (2013.01); *C12Q 1/689* (2013.01); *A23V 2002/00* (2013.01); *A61K 2035/11* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 7,344,867 B2 | 3/2008 | Connolly |
| 2008/0254011 A1 | 10/2008 | Rothschild et al. |

FOREIGN PATENT DOCUMENTS

| | | |
|---|---|---|
| EP | 1918373 A1 | 5/2008 |
| EP | 2604689 A1 | 6/2013 |
| WO | WO 2003105893 A2 | 12/2003 |
| WO | WO 2006110088 A1 | 10/2006 |
| WO | WO 2008028300 A1 | 3/2008 |

OTHER PUBLICATIONS https://www.nidcr.nih.gov/OralHealth/Topics/GumDiseases/PeriodontalGumDisease.htm retrieved Mar. 14, 2007.*
http://www.atcc.org/products/all/PTA-6475.aspx: Lactobacillus reuteri (isolated from human mother's milk . . . .
Boyce, F.B. et al., TNFalpha and pathologic bone resorption, Keio J Med. 54(3): 127-131, 2005.
Britton, R.A. et al., Probiotic L. reuteri treatment prevents bone loss in a menopausal ovariectomized mouse model, J. Cell. Physiol. 229: 1822-1830, 2014.
Iyer, C. et al., Probiotic Lactobacillus reuteri promotes TNF-induced apoptosis in human myeloid leukemia-derived cells . . . , Cell. Microbiol. 10(7): 1442-1452, 2008.
Kim, J.G. et al., Effects of a Lactobacillus casei 393 fermented milk product on bone metabolism in ovariectomised rats, Int. Dairy J. 19: 690-695, 2009.
Lai, C-Y et al., Preventing bone loss and weight gain with combinations of vitamin D and phytochemicals, J. Med. Food 14(11): 1352-1362, 2011.
McCabe, L.R., Probiotics and bone health—role of gender and intestinal health, NIH Office of Dietary Supplements, Grant abstact, publication date unknown.
McCabe, L.R. et al., Probiotic use decreases intestinal inflammation and increases bone density in healthy male but not . . . , J. Cell Physiol. 228:1793-1798, 2013 online.
Morita, H. et al., Comparative genome analysis of lactobacillus reuteri and lactobacillus fermentum reveal . . . , DNA Research 15: 151-161, 2008.
Scholz-Ahrens, K.E. et al., Prebiotics, probiotics, and synbiotics affect mineral absorption, bone mineral content . . . , J. Nutr., 137: 838S-846S, 2007.

* cited by examiner

*Primary Examiner* — Oluwatosin A Ogunbiyi
(74) *Attorney, Agent, or Firm* — Lynn E. Barber

(57) ABSTRACT

The present invention comprises a method for selecting lactic acid bacterial strains effective for preventing bone loss in humans and strains that have been selected according to the presented method. The selection method is based on the strain's capability of reestablishing an altered microbial community to normal and/or harboring at least one of four specific SNPs.

1 Claim, 3 Drawing Sheets

SELECTION AND USE OF LACTIC ACID BACTERIA PREVENTING BONE LOSS IN MAMMALS

GOVERNMENT RIGHTS

This invention was made with government support under AT005472 awarded by the National Institutes of Health. The government has certain rights in the invention.

FIELD OF THE INVENTION

The present invention relates generally to medicine, pharmacology and food supplements. More specifically the invention relates to selection and use of lactic acid bacteria for the prevention of bone loss in mammals.

BACKGROUND OF THE INVENTION

Over 40 million Americans over the age of 50 (14 million of which are men) are afflicted with low bone density or osteoporosis and its associated increased risk of fractures. Individuals with osteoporotic fractures are prone to depression, dependency and increased mortality. While aging is a major cause of osteoporosis, disease, disuse, and certain drugs can also cause bone loss at any stage in life.

The skeleton is a highly organized system that supports the body's weight, houses mesenchymal and hematopoetic stem cells, and serves as a calcium reservoir. The structure of bone comprises an outer cortical dense shell and an inner trabecular bone meshwork. Exercise can increase trabecular bone mineral density (BMD), and bone volume fraction (BVF), trabeculi thickness, and cortical BMD and thickness. In contrast, disease, disuse, and certain drugs (such as glucocorticoids) can decrease these parameters and cause osteoporosis in both males and females. Osteoporosis is defined by a reduction in bone mass (more than 2.5 standard deviations (SD) below average) and altered bone microarchitecture (such as decreased trabeculi thickness). With decreasing bone mass there is an increased risk of bone fractures. Thus, at the point of being diagnosed as osteoporotic, a patient has a 16-fold increase in fracture risk compared to someone with normal bone density. Fractures are associated with depression, dependency, and increased mortality (greater than 25% within 12 months for the elderly) and hip fractures account for over 50,000 deaths annually (National Osteoporosis Foundation (NOF) statistic). While osteoporosis is less prevalent in men, over 30% of hip fractures occur in men and mortality rates are greater for males compared to females. Currently, over 20 billion dollars are spent in the US and 30 billion dollars in the European Union to cover the direct costs of osteoporosis. Of even greater concern, it is estimated that by 2020 more than 61 million men and women in the US, over the age of 50, will have low bone density or osteoporosis (NOF statistic), and finding effective novel treatments is therefore a priority. In fact, one in three women over the age of 50 will experience an osteoporosis related fracture in their lifetime. Along with its associated increase in fracture risk, bone loss may have negative effects on metabolism and insulin secretion. Despite all the available treatments on the market, the number of osteoporotic patients is on the rise in the U.S. and worldwide. There are several reasons for this, including a lack of awareness that one is at risk early in life, an increasing elderly population, and patient noncompliance due to unwanted medication side effects. In addition, conventional bone loss treatments are not always effective.

Currently there are no alternative or natural treatments that can be used in place of osteoporosis medicines for people with low bone density or osteoporosis. Therefore, doctors are looking for new approaches to increase bone density in their patients and companies are working to improve pharmacologic bone therapeutic drugs.

Certain people are more likely to develop osteoporosis than others, some risk factors are:
Being female
Older age
Family history of osteoporosis or broken bones
Being small and thin
Certain race/ethnicities such as Caucasian, Asian, or Hispanic/Latino although African Americans are also at risk
History of broken bones
Low levels of sex hormones
Low estrogen levels in women, including menopause
Missing periods (amenorrhea)
Low levels of testosterone and estrogen in men
Diet
   Low calcium intake
   Low vitamin D intake
   Excessive intake of protein, sodium and caffeine
Inactive lifestyle
Smoking
Alcohol abuse
Certain medications such as steroid medications, some anticonvulsants and others
Certain diseases and conditions such as anorexia nervosa, rheumatoid arthritis, gastrointestinal diseases and others Menopausal women are prone to losing bone during menopause time due to decreased estrogen levels. Even during perimenopause (the period of 2 to 8 years before menopause) estrogen levels may start to drop off. Over time, too much bone loss can first cause osteopenia (low bone mass) and then osteoporosis.

Diagnosis of type 1 diabetes (T1D) is increasing in children and adults. While medical advances are extending patient lifespan, maintaining euglycemia remains difficult, even under therapeutic vigilance. Thus, more T1D patients (males and females) are suffering from complications, including bone loss. This means that patients begin aging/menopause with an already increased fracture risk. Once fractures occur, they can be difficult to heal, require extended hospitalizations, reduce the quality of life and increase mortality. Poor bone health also negatively affects the entire body. Postmenopausal women with T1D diabetes have higher incidences of osteoporotic fractures than women without diabetes. Children with T1D have lower bone mineral density than children without diabetes. Thus, maintaining bone health is critical for the overall quality of life of T1D patients and important for maximizing therapeutic/curative treatments involving marrow immune/progenitor cells since marrow cells and bone cells communicate.

Type 2 Diabetes (T2D) patients are also at higher risk of osteoporotic fractures than non-diabetics.

The two key components to strengthening bone and preventing osteoporosis are 1) attaining maximum bone density and 2) preventing bone loss during adulthood and aging. Bone remodeling occurs because bone is dynamic and constantly adapts to environmental cues to form or resorb bone. Targeted bone remodeling through the activities of osteoblasts (bone forming cells) and osteoclasts (bone resorbing cells) maintains blood calcium levels within a critical range while keeping bone strong at sites where support is needed. When formation and resorption activities are in balance there is no net gain or loss of bone, however when formation is decreased and/or resorption is increased then bone loss ensues.

Increased osteoclast activity results in bone resorption. Osteoclasts are derived from hematopoetic stem cells. These cells give rise to cells of the monocyte/macrophage lineage which, under the right conditions, develop into osteoclast precursors. Further signaling through factors such as RANKL (located on osteoblast surfaces) stimulate osteoclast maturation. Mature osteoclasts express enzymes involved in bone matrix degradation (including cathepsin K and TRAP5b).

Increased osteoblast activity results in bone formation, which can be regulated at several levels including 1) lineage selection, 2) maturation and 3) death. Because bone marrow stromal cells (BMSC) give rise to osteoblasts, adipocytes and other cell types, selection of one lineage (adipocyte) could be at the cost of another (osteoblast). This is supported by the reciprocal relationship between bone adiposity and mineral density recognized with aging, limb unloading, cell culture models, and type I (T1) diabetes. Osteoblast activity can be further regulated through death/apoptosis. An increase in osteoblast death will result in fewer bone making cells and therefore bone loss. Examples include the rapid bone adaptation to disuse/unloading, which results in bone loss, increased marrow adiposity, and increased bone cell death. Aging also increases bone cell apoptosis. Many factors contribute to modulating some or all aspects of osteoblast regulation (lineage, maturation, death) including: positive factors such as TGFβ, bone morphogenic proteins (BMPs), parathyroid hormone (PTH), and Wnts and negative factors such as cytokines.

Bisphosphonates are one of the most common treatments for osteoporosis. These compounds incorporate into the bone mineral and inhibit bone catabolism by osteoclasts and are effective at reducing fractures. However, many of these compounds need to be taken on an empty stomach and can cause gastric reflux and nausea resulting in reduced patient compliance. There is also concern about the length of time that these compounds reside in bone and their long-term impact on bone remodeling and strength. Selective estrogen receptor modifiers (SERMS) are another therapeutic treatment, but they still carry some concerns with regard to cancer. Hormone replacement therapy has been studied as useful in preventing or slowing the occurrence of osteoporosis, but sustained use of hormone replacement over many years may increase women's risk of breast cancer, may increase incidence of venous thrombosis (blood clots), exacerbation of pre-existing liver diseases and an increased risk of endometrial cancer as well as hypertension. Amgen has a drug under development (that is similar to osteoprotegrin) that works by modifying the RANKL/RANK system and hence suppresses osteoclast activity. Intermittent PTH treatment is an anabolic treatment, but this intravenous treatment is expensive and only indicated for severe osteoporotic patients. Taken together, it is not surprising that many people diagnosed with low bone density are confused about what to do. Many people do not want to take medication for fear of long-term effects. While weight bearing exercise and adequate calcium intake are two natural approaches, they cannot always overcome effects of disease, medications, and aging.

SUMMARY OF THE INVENTION

A primary object of the present invention is to provide a method how to find a lactic acid bacterial strain that may prevent bone loss, especially in menopausal women, in diabetics, and in osteopenic people, which includes for example young men with large energy intake and low exercise frequency.

An object of the present invention is to use products containing such strains in menopausal women to prevent bone loss.

An object of the present invention is to use products containing such strains in women who have had a hysterectomy to prevent bone loss.

Another object is to use products containing such strains in men, including but not limited to diabetic, young men with metabolic disturbance and osteopenic men, to prevent bone loss.

Another object is to use such product in combination with therapies for bone loss or bone formation in order to reduce the dose of such drugs to be able to minimize side effects.

Another object is to improve bone repair after fracture.

Accordingly, a first aspect of the invention provides a method for selecting a lactic acid bacterial strain for use in preventing or treating bone loss, comprising selecting a lactic acid bacterial strain having at least 95% identity to the genome of *L reuteri* JCM 1112 (SEQ ID NO: 1), and harboring an identical nucleotide relative to the genome of *L reuteri* JCM 1112 (SEQ ID NO: 1) in at least one of the following four positions: C in base pair 271 391, G in base pair 453 538, G in base pair 529 228, and C in base pair 599 338.

In an embodiment according to the first aspect, the method comprises selecting a lactic acid bacterial strain having at least 96%, such as 97%, such as 98%, such as 99% identity to the genome of *L reuteri* JCM 1112 (SEQ ID NO: 1), and harboring an identical nucleotide relative to the genome of *L reuteri* JCM 1112 (SEQ ID NO: 1) in at least one of the following four positions: C in base pair 271 391, G in base pair 453 538, G in base pair 529 228, and C in base pair 599 338.

A second aspect of the invention provides a method for selecting a lactic acid bacterial strain, such as a *Lactobacillus reuteri* strain, for use in preventing or treating bone loss, comprising selecting a *Lactobacillus reuteri* harboring an identical nucleotide relative to the genome of *L reuteri* JCM 1112 (SEQ ID NO: 1) in at least one of the following four positions: C in base pair 271 391, G in base pair 453 538, G in base pair 529 228, and C in base pair 599 338.

In an embodiment of the method according to the first or second aspect, the lactic acid bacterial strain harbors at least two of said four nucleotides, such as at least three of said four nucleotides, such as all four of said nucleotides.

A third aspect of the invention provides a method for selecting a lactic acid bacterial strain for use in preventing or treating bone loss, comprising selecting a lactic acid bacterial strain having at least 95% identity to the genome of *L reuteri* JCM 1112 (SEQ ID NO: 1), provided that the lactic acid bacterial strain does not harbor at least one mutation relative to the genome of *L reuteri* JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the third aspect, the method comprises selecting a lactic acid bacterial strain having at least 96%, such as 97%, such as 98%, such as 99% identity to the genome of *L reuteri* JCM 1112 (SEQ ID NO: 1), provided that the lactic acid bacterial strain does not harbor at least one mutation relative to the genome of *L reuteri* JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the method according to the third aspect, the lactic acid bacterial strain does not harbor at least two of said four mutations, such as at least three of said four mutations, such as anyone of said four mutations.

A fourth aspect of the invention provides a lactic acid bacterial strain, selected according to the method according to the first, second or third aspect, for use in the prevention or treatment of bone loss.

In an embodiment of the fourth aspect, the lactic acid bacterial strain selected is *L reuteri* ATCC PTA 6475, for use in the prevention or treatment of bone loss. This strain is available to the public at the American Type Culture Collection (10801 Univ. Blvd., Manassas, Va.), having been deposited there under the Budapest Treaty on Dec. 21, 2004.

According to a fifth aspect, the invention provides a lactic acid bacterial strain having at least 95% identity to the genome of *L reuteri* JCM 1112 (SEQ ID NO: 1), and harboring an identical nucleotide relative to the genome of *L reuteri* JCM 1112 (SEQ ID NO: 1) in at least one of the following four positions: C in base pair 271 391, G in base pair 453 538, G in base pair 529 228, and C in base pair 599 338, for use in the prevention or treatment of bone loss.

In an embodiment of the fifth aspect, the lactic acid bacterial strain has at least 96%, such as 97%, such as 98%, such as 99% identity to the genome of *L reuteri* JCM 1112 (SEQ ID NO: 1), and harbors an identical nucleotide relative to the genome of *L reuteri* JCM 1112 (SEQ ID NO: 1) in at least one of the following four positions: C in base pair 271 391, G in base pair 453 538, G in base pair 529 228, and C in base pair 599 338.

In an embodiment of the fifth aspect, the lactic acid bacterial strain harbors at least two of said four nucleotides, such as at least three of said four nucleotides, such as all four of said nucleotides.

According to a sixth aspect, the invention provides a lactic acid bacterial strain having at least 95% identity to the genome of *L reuteri* JCM 1112 (SEQ ID NO: 1), provided that the lactic acid bacterial strain does not harbor at least one mutation relative to the genome of *L reuteri* JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the sixth aspect, the lactic acid bacterial strain has at least 96%, such as 97%, such as 98%, such as 99% identity to the genome of *L reuteri* JCM 1112 (SEQ ID NO: 1), provided that the lactic acid bacterial strain does not harbor at least one mutation relative to the genome of *L reuteri* JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the sixth aspect, the lactic acid bacterial strain does not harbor at least two of said four mutations, such as at least three of said four mutations, such as anyone of said four mutations.

According to a presently preferred embodiment of the fifth or sixth aspect, the lactic acid bacterial strain is *L reuteri* ATCC PTA 6475.

A seventh aspect of the invention provides a composition comprising a lactic acid bacterial strain selected according to the method according to the first, second, or third aspect of the invention.

According to an eighth aspect, a composition is provided comprising a lactic acid bacterial strain having at least 95% identity to the genome of *L reuteri* JCM 1112 (SEQ ID NO: 1), and harboring an identical nucleotide relative to the genome of *L reuteri* JCM 1112 (SEQ ID NO: 1) in at least one of the following four positions: C in base pair 271 391, G in base pair 453 538, G in base pair 529 228, and C in base pair 599 338.

In an embodiment of the eighth aspect, the lactic acid bacterial strain has at least 96%, such as 97%, such as 98%, such as 99% identity to the genome of *L reuteri* JCM 1112 (SEQ ID NO: 1), and harbors an identical nucleotide relative to the genome of *L reuteri* JCM 1112 (SEQ ID NO: 1) in at least one of the following four positions: C in base pair 271 391, G in base pair 453 538, G in base pair 529 228, and C in base pair 599 338.

In an embodiment of the eighth aspect, the lactic acid bacterial strain harbors at least two of said four nucleotides, such as at least three of said four nucleotides, such as all four of said nucleotides.

According to a ninth aspect, the invention provides a composition comprising a lactic acid bacterial strain having at least 95% identity to the genome of *L reuteri* JCM 1112 (SEQ ID NO: 1), provided that the lactic acid bacterial strain does not harbor at least one mutation relative to the genome of *L reuteri* JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the ninth aspect, the lactic acid bacterial strain has at least 96%, such as 97%, such as 98%, such as 99% identity to the genome of *L reuteri* JCM 1112 (SEQ ID NO: 1), provided that the lactic acid bacterial strain does not harbor at least one mutation relative to the genome of *L reuteri* JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the ninth aspect, the lactic acid bacterial strain does not harbor at least two of said four mutations, such as at least three of said four mutations, such as anyone of said four mutations.

In a presently preferred embodiment of the eighth or ninth aspect, the lactic acid bacterial strain is *L reuteri* ATCC PTA 6475.

In an embodiment of the eighth or ninth aspect, the composition is for use in the prevention or treatment of bone loss.

In another embodiment of the eighth or ninth aspect, the composition is for use in preventing bone loss in menopausal women, women who have had hysterectomy, diabetics, osteopenic individuals, osteoporotic individuals, and individuals with metabolic disturbance.

In yet another embodiment of the eighth or ninth aspect, the composition is for use in improving bone repair after fracture.

In an embodiment of the eighth or ninth aspect, the above-described composition in combination with vitamin D is for use in preventing or treating bone loss.

In another embodiment of the eighth or ninth aspect, the above-described composition in combination with a hormone (for use in hormone replacement therapy) is for use in preventing or treating bone loss.

In an embodiment of the eighth or ninth aspect, the above-described composition is a pharmaceutical composition (optionally comprising at least one pharmaceutically acceptable excipient), or a food product or a food supplement (optionally comprising at least one food-grade excipient, as known to a person of ordinary skill in the art).

According to a tenth aspect, the invention provides a use of a lactic acid bacterial strain having at least 95% identity to the genome of L reuteri JCM 1112 (SEQ ID NO: 1), and harboring an identical nucleotide relative to the genome of L reuteri JCM 1112 (SEQ ID NO: 1) in at least one of the following four positions; C in base pair 271 391, G in base pair 453 538, G in base pair 529 228, and C in base pair 599 338, for the manufacture of a pharmaceutical composition for the prevention or treatment of bone loss.

In an embodiment of the tenth aspect, the lactic acid bacterial strain has at least 96%, such as 97%, such as 98%, such as 99% identity to the genome of L reuteri JCM 1112 (SEQ ID NO: 1), and harbors an identical nucleotide relative to the genome of L reuteri JCM 1112 (SEQ ID NO: 1) in at least one of the following four positions: C in base pair 271 391, G in base pair 453 538, G in base pair 529 228, and C in base pair 599 338.

In an embodiment of the tenth aspect, the lactic acid bacterial strain harbors at least two of said four nucleotides, such as at least three of said four nucleotides, such as all four of said nucleotides.

According to an eleventh aspect, the invention provides a use of a lactic acid bacterial strain having at least 95% identity to the genome of L reuteri JCM 1112 (SEQ ID NO: 1), provided that the lactic acid bacterial strain does not harbor at least one mutation relative to the genome of L reuteri JCM 1112 (SEQ ID NO: 1), selected from the group of four mutations consisting of C to T in base pair 271 391, G to A in base pair 453 538, G to A in base pair 529 228, and C to T in base pair 599 338, for the manufacture of a pharmaceutical composition for the prevention or treatment of bone loss.

In an embodiment of the eleventh aspect, the lactic acid bacterial strain has at least 96%, such as 97%, such as 98%, such as 99% identity to the genome of L reuteri JCM 1112 (SEQ ID NO: 1), provided that the lactic acid bacterial strain does not harbor at least one mutation relative to the genome of L reuteri JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the eleventh aspect, the lactic acid bacterial strain does not harbor at least two of said four mutations, such as at least three of said four mutations, such as anyone of said four mutations.

In a presently preferred embodiment of the tenth or eleventh aspect, the lactic acid bacterial strain is L reuteri ATCC PTA 6475.

A twelfth aspect of the invention provides a method for the treatment or prevention of bone loss, comprising administering, to an individual, a lactic acid bacterial strain having at least 95% identity to the genome of L reuteri JCM 1112 (SEQ ID NO: 1), and harboring an identical nucleotide relative to the genome of L reuteri JCM 1112 (SEQ ID NO: 1) in at least one of the following four positions: C in base pair 271 391, G in base pair 453 538, G in base pair 529 228, and C in base pair 599 338.

In an embodiment of method according to the twelfth aspect, the lactic acid bacterial strain has at least 96%, such as 97%, such as 98%, such as 99% identity to the genome of L reuteri JCM 1112 (SEQ ID NO: 1), and harbors an identical nucleotide relative to the genome of L reuteri JCM 1112 (SEQ ID NO: 1) in at least one of the following four positions: C in base pair 271 391, G in base pair 453 538, G in base pair 529 228, and C in base pair 599 338.

In an embodiment of the twelfth aspect, the lactic acid bacterial strain harbors at least two of said four nucleotides, such as at least three of said four nucleotides, such as all four of said nucleotides.

According to a thirteenth aspect, the invention provides a method for the treatment or prevention of bone loss, comprising administering, to an individual, a lactic acid bacterial strain having at least 95% identity to the genome of L reuteri JCM 1112 (SEQ ID NO: 1), provided that the lactic acid bacterial strain does not harbor at least one mutation relative to the genome of L reuteri JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the thirteenth aspect, the lactic acid bacterial strain has at least 96%, such as 97%, such as 98%, such as 99% identity to the genome of L reuteri JCM 1112 (SEQ ID NO: 1), provided that the lactic acid bacterial strain does not harbor at least one mutation relative to the genome of L reuteri JCM 1112 (SEQ ID NO: 1), selected from the group of four mutations consisting of C to T in base pair 271 391, G to A in base pair 453 538, G to A in base pair 529 228, and C to T in base pair 599 338.

In an embodiment of the thirteenth aspect, the lactic acid bacterial strain does not harbor at least two of said four mutations, such as at least three of said four mutations, such as anyone of said four mutations.

In a presently preferred embodiment of the twelfth or thirteenth aspect, the lactic acid bacterial strain is L reuteri ATCC PTA 6475.

DETAILED DESCRIPTION OF THE INVENTION AND PREFERRED EMBODIMENTS THEREOF

Figure 1:
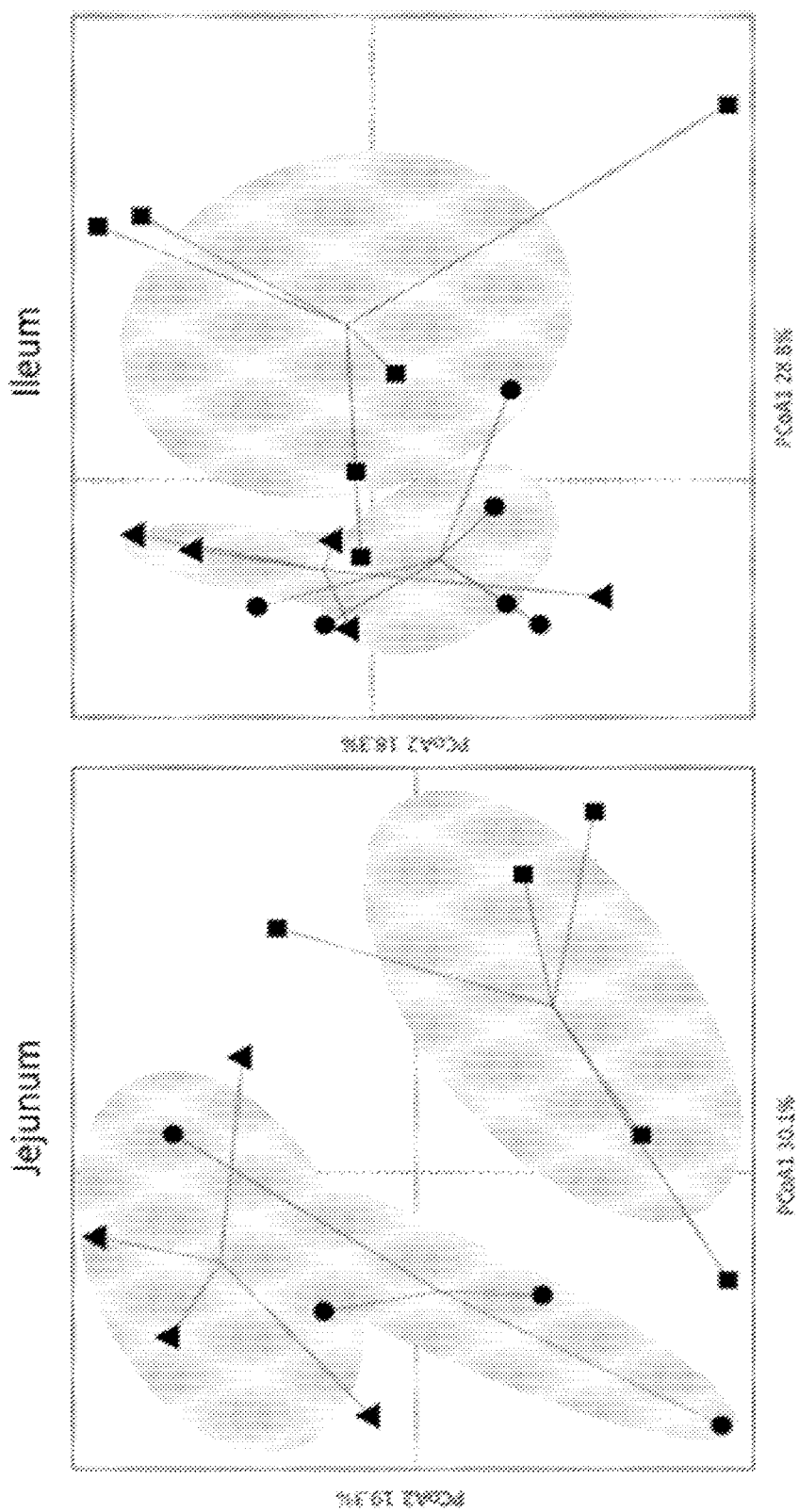
FIG. 1 shows microbial community clustering in jejunum and ileum.

No prior art either alone or in combination teaches how one can select specific probiotic strains that are effective for preventing bone loss.

The present invention herein comprises a method for selecting lactic acid bacterial strains effective for preventing bone loss in humans and strains that have been selected according to the presented method. Products such as foods, nutritional additives and formulations, pharmaceuticals or medical devices containing whole cells or components derived from these strains may be formulated as is known in the art, and generally include an ingestible support as known plus the lactic acid bacterial strain, or its derived component.

Based on prior art it would be natural to think that a strain's capability of preventing bone loss would be associated with its general effect on intestinal health or its anti-inflammatory properties, however the inventors have surprisingly found out that these properties are not predictive on the efficiency on preventing bone loss. Lactobacillus reuteri ATCC PTA 6475 and Lactobacillus reuteri ATCC PTA 4659 are two almost identical strains, which are both anti-inflammatory and improve overall intestinal health. It is natural to assume that these strains therefore would have the same effect on bone loss as well. However the inventors have shown that these strains do not have the same impact on preventing bone loss and based on this observation they have invented a novel way of selecting lactic acid bacterial strains, such as for example *Lactobacillus reuteri* that will be effective for treatment and/or prevention of bone loss.

Lactic acid bacteria specifically selected by the method presented herein may be administered to humans to prevent bone loss.

*L. reuteri* ATCC PTA 6475 and ATCC PTA 4659 differ in four SNPs, which are important for the bacteria's ability to prevent bone loss. These SNPs are shown in Walter et al. (Walter et al. *Host-microbial symbiosis in the vertebrate gastrointestinal tract and the Lactobacillus reuteri paradigm*; PNAS, vol. 108 p. 4645-4652), which is hereby fully incorporated by reference. For the SNP analysis, sequencing results were mapped onto a reference genome (*L. reuteri* JCM 1112, GenBank accession no AP007281, SEQ ID NO: 1). Seven SNPs were found in *L. reuteri* ATCC PTA 4659, and three of them were also found in *L. reuteri* ATCC PTA 6475 (SNP 4 located at bp 567 368, SNP 6 located at bp 968 088, and SNP 8 located at bp 1 358 460, referring to the reference genome, *L. reuteri* JCM 1112, GenBank accession no AP007281, SEQ ID NO: 1). The remaining four unique SNPs (for the purpose of the present text, hereinafter called SNP 1, SNP 2, SNP 3 and SNP 5, respectively) constitute the genomic differences between *L. reuteri* ATCC PTA 6475 and *L. reuteri* ATCC PTA 4659. Said four SNPs are located at:

bp 271 391 (SNP 1),
bp 453 538 (SNP 2),
bp 529 228 (SNP 3), and
bp 599 338 (SNP 5), (referring to the reference genome, *L. reuteri* JCM 1112, GenBank accession no AP007281; SEQ ID NO: 1).

SNP 1 is located in a gene coding for a conserved hypothetical protein (*L. reuteri* JCM 1112: http://www.ncbi.nlm.nih.gov/protein/183224225), SNP 2 is located in a gene coding for a chloride channel protein (*L. reuteri* JCM 1112: http://www.ncbi.nlm.nih.gov/protein/183224386), SNP 3 is located in a gene coding for an ATP synthase gamma subunit (*L. reuteri* JCM 1112: http://www.ncbi.nlm.nih.gov/protein/183224455) and SNP 5 is located in a gene coding for a DNA mismatch repair protein HexB (*L. reuteri* JCM 1112: http://www.ncbi.nlm.nih.gov/protein/183224511). The SNPs involved in this invention are the ones that match *L. reuteri* ATCC PTA 6475, the sequence of which has identical nucleotides as *L. reuteri* JCM 1112 in the positions of SNP 1, SNP 2, SNP 3 and SNP 5). Listed below are the nucleotides that differ between the strains *L. reuteri* ATCC PTA 6475 and 4659:

SNP 1) a gene coding for a hypothetical protein, where nucleotide 267 has been changed in ATCC PTA 4659 from a C (as in ATCC PTA 6475 and JCM 1112) to a T.

SNP 2) the gene coding for the chloride channel protein, where nucleotide 373 has been changed in ATCC PTA 4659 from a G (as in ATCC PTA 6475 and JCM 1112) to an A.

SNP 3) the gene coding for ATP synthase gamma subunit, where nucleotide 296 has been changed in ATCC PTA 4659 from a G (as in ATCC PTA 6475 and JCM 1112) to an A.

SNP 5) the gene coding for the HexB protein, where nucleotide 1966 has been changed from a C (as in ATCC PTA 6475 and JCM 1112) to a T.

In the selection method of this invention, strains are sought that, in at least one of these SNPs, harbor the same nucleotides as *L. reuteri* ATCC PTA 6475 for the above mentioned SNPs.

The microbiota plays an important role in bone loss; many patients suffering from bone loss have a disturbed intestinal microbiota. Lactic acid bacteria that are able to reestablish the normal microbial community in the GI tract are surprisingly more effective in preventing bone loss.

The present invention discloses a unique method of selection, selecting strains effective for preventing bone loss. The ability to reestablish the total gut microbial composition is surprisingly also important for the function in preventing bone loss. The inventors have found out that strains capable of reestablishing an altered microbial community to normal and/or harboring at least one of the four specific SNPs are effective for preventing bone loss.

The ability to prevent bone loss is unique for certain strains and is not at all general for all lactic acid bacteria. When selecting effective strains it is not sufficient to use anti-inflammatory capacity as selection criteria since the inventors clearly show that this effect is not dependent on anti-inflammatory features. *L. reuteri* ATCC PTA 6475 and *L. reuteri* ATCC PTA 4659 are both anti-inflammatory strains, but *L. reuteri* ATCC PTA 6475 is much more effective when used for prevention of bone loss, and *L. reuteri* ATCC PTA 4659 is not selected according to this invention. Specific lactic acid bacterial strains selected according to the present invention may be used for preventing bone loss in general and the embodiments below are not intended to limit the scope of this invention, but to exemplify preferred embodiments.

Vitamin D is crucial to bone health and people with low levels of vitamin D have lower bone density or bone mass. People that do not get enough vitamin D may lose bone, since vitamin D is required to absorb calcium. The inventors have seen that an altered microbiota will lead to vitamin D deficiency and bone loss. Administration of lactic acid bacteria selected according to the present invention will reestablish the microbiota and thereby increase the intestinal vitamin D absorption and restore the levels of vitamin D. It is also an option to combine vitamin D with the selected strains in order to get an even more efficient method/product for preventing bone loss.

T1D patients suffer from complications such as bone loss. Patients suffering from T1D will as a result of the condition have an altered microbiota. Administration of lactic acid bacteria selected according to the present invention will reestablish the microbiota and prevent bone loss.

High bone density during youth and adulthood can help prevent diseases like osteoporosis later in life. This is due to the fact that high bone density will allow a higher degree of bone loss before reaching a bone density within the osteoporosis zone. Thus, it is an object of the present invention to prevent bone loss by administering lactic acid bacterial strains, selected according to the present invention, to young and adult people. This will help individuals to obtain maximum bone density to prevent osteoporosis from occurring later in life. Administration of lactic acid bacteria selected according to the present invention prevents bone loss in healthy recipient as well as those suffering from bone loss.

Administration of selected lactic acid bacteria may be combined with hormone replacement therapy. Such a combination would make it possible to reduce the amount of hormones and thereby reduce the side effects, such as reducing the risk of cancer.

Lactic acid bacteria selected for preventing bone loss would preferably be administered to menopausal women and osteopenic men who are prone to develop osteoporosis, and administration of selected lactic acid bacteria will prevent bone loss and thus preventing low bone density and osteoporosis.

The inventors have seen that estrogen depletion alters the gut microbiota. Treatment with lactic acid bacteria selected according to the present invention will reestablish the microbiota in people suffering from decreased estrogen levels, including but not limited to menopausal women and women who had hysterectomy, consequently preventing bone loss.

Lactic acid bacterial strains selected according to the present invention may also be used to improve fracture repair.

In order to reduce side effects of drugs, such as for example bisphosphonates and hormone replacement therapy used to treat bone loss it is possible to combine drugs with administration of selected lactic acid bacteria and thereby reduce the dose, which will minimize the side effects.

Example 1

Study of *L. reuteri* ATCC PTA 6475's Ability to Reestablish Altered Microbial Communities in ovx Mice.

There are significant changes in the intestinal microbial communities of control (non-ovx), ovx and ovx fed by *L. reuteri*.

Experimental Groups and Tissue Collection.

In order to measure the effects of ovariectomy (ovx) and *L. reuteri* 6475 treatment of ovx mice we compared three experimental groups of animals. Control mice were non-ovx mice that received a vehicle control gavage three times per week. Ovx mice received a vehicle control gavage three times per week. Ovx+*L. reuteri* 6475 were mice that received 300 µl of overnight *L. reuteri* 6475 three times per week for four weeks. At the end of the experiment mice were euthanized and tissue samples from the stomach, duodenum, jejunum, ileum, proximal and distal colons were isolated and saved for microbial ecology analysis.

DNA Extraction

Murine intestinal tissue was placed in MoBio Ultra Clean Fecal DNA Bead Tubes (cat.#12811-100-DBT) containing 360 µl Buffer ATL (Qiagen cat.#19076) and lysed on a Mini-Beadbeater-8 (BioSpec Products) for 1 minute at full speed. DNA was extracted from murine intestinal tissue using Qiagen DNeasy Blood and Tissue kit (cat.#69504). The tissue was further disrupted by adding 40 µl proteinase K (Qiagen, cat.#19133) and incubating at 55° C. for 1 hour. DNA was extracted using the Qiagen DNeasy Blood and Tissue kit (cat.#69504). DNA yield was quantified using a Nanodrop 1000.

PCR Amplification

Bacterial 16S sequences were amplified for 454 sequencing from murine intestinal tissue using the V3-V5 barcoded primer set and amplification protocol developed by the Broad Institute for the Human Microbiome Project. Barcoded forward primers were synthesized by IDT DNA Technologies and the reverse primer was synthesized by Sigma. Barcoded forward primers were diluted to a working concentration of 4 µM in 96 well plates; the reverse primer was added to each well to a final concentration of 4 µM. Triplicate reactions in a 25 µl volume were prepared containing 400 µg murine intestinal DNA, 2 µl 4 µM primers, and 0.15 µl Accuprime HiFi Taq polymerase in 1× Accuprime Buffer II (Invitrogen, cat.#12346086). Reactions were amplified in an Eppendorf Pro aluminum plate thermal cycler with a 2 minute 95° C. denaturation, followed by 30 cycles of 95° C.×20 sec, 50° C.×30 sec, 72° C.×5 min.

Amplification Product Purification 16S amplification products were purified using Ampure Agencourt XP beads (Beckman Coulter, cat# A63880). First, triplicate reactions for each sample were combined into 1.7 ml microfuge tubes and Ampure XP beads were added at a 0.7× volume ratio. After vortexing, the mixed samples were incubated for 10 minutes at room temperature then placed on a magnetic stand to separate the beads (Invitrogen, cat.#123-21D). The beads were washed according to the manufacturer's protocol with 2 washes of 200 µl of 70% ethanol. The beads were dried at 37° C. for 5 minutes, and DNA was eluted with 20 µl 10 µM Tris buffer/0.1 µM EDTA. The eluent was separated from the beads on the magnetic stand, transferred to a new 1.7 ml microfuge tube, and quantified using the using the Quant-It dsDNA high-sensitivity assay kit (Invitrogen, cat# Q33120). Equal amounts of each sample were then pooled into one tube for 454 sequencing.

454 Sequencing and Sequence Analysis 454 sequencing was performed using the GS Junior (Roche) using Titanium chemistry. In addition to the standard filters utilized by the GS Jr. to identify passed reads we utilized a modified amplicon processing algorithm to reduce the number of incorrectly discarded sequences. 16S rRNA sequences were aligned by the Ribosomal Database Project staff at MSU to *E. coli* 16S sequences and trimmed at *E. coli* 16S nucleotide positions 617 to 900. Subsequent processing and analysis (including diversity metrics) were performed using MOTHUR v.1.21 (http://www.mothur.org/wiki/). ANOSIM (analysis of similarity) and principle coordinate analysis were performed using the software package PAST. The accompanying figures and table utilize the Bray-Curtis method for measuring the level of dissimilarity between two or more microbial communities. In these analyses we chose an operational taxonomic unit (OUT) cutoff of 0.03, which is considered to be viewing the communities at the species level. From these data we conclude that in that treatment of ovariectomized mice with *L. reuteri* ATCC PTA 6475 causes a significant shift in the both the ileal and jejunal microbial communities, which correlates with improved bone health. (ovx+lacto in the table 1).

TABLE 1

ANOSIM analysis at species level using Bray-Curtis dissimilarity matrix, ** indicates statistical significance.

| Tissue | Comparison | R Value (p value) |
| --- | --- | --- |
| Jejunum | wt-ovx-ovxlacto | 0.3367 (0.0183)* |
| | wt-ovx | 0.0443 (0.3633) |
| | wt-ovxlacto | 0.6078 (0.0250)* |
| | ovx-ovxlacto | 0.3297 (0.0712) |
| Ileum | wt-ovx-ovxlacto | 0.2068 (0.0084)* |
| | wt-ovx | 0.1710 (0.1180) |
| | wt-ovxlacto | 0.2540 (0.0290)* |
| | ovx-ovxlacto | 0.2209 (0.0206)* |

Three-way comparison of the wild-type, ovx, and ovx treated with *L. reuteri* showed significant shifts in microbial communities (table 1). These differences are largely driven by substantial shifts in communities after *L. reuteri* treatment. Principle coordinate analysis of microbial communities from the wild-type control group (triangle Δ), ovx group (circle ●) and the ovx group treated with *L. reuteri* (square ■) was used to visualize how communities clustered in the jejunum and the ileum. FIG. 1 shows that ovx mice treated with *L. reuteri* form a cluster of communities that is distinct from wild-type and ovx communities in both the jejunum and ileum. Several OTUs that were classified as Clostridriales are the main groups of bacteria that are driving the separation of the L. reuteri treated Ovx communities from the other two groups.

Example 2

Study of L. reuteri ATCC PTA 4659's Ability to Reestablish Altered Microbial Communities in ovx Mice.

The experiment is performed as in example 1, but L. reuteri ATCC PTA 4659 is used instead of L. reuteri ATCC PTA 6475.

L. reuteri ATCC PTA 4659 treatment is not able to restore ovx communities toward control.

Example 3

Identification of Certain SNPs
Illumina Sequencing of L. reuteri Genomes

L. reuteri strains used in this study were ATCC PTA 4659 and 6475 grown in MRS media (Difco) and genomic DNA prepared by using the Qiagen Genomic-Tip System. DNA was fragmented by 20 min sonication (130 W) to obtain an average fragment size of 500 bp, then further purified and concentrated with QIAquick PCR Purification Spin Columns (Qiagen). Treatment to remove 3' over-hangs and fill in 5' overhangs resulted in blunt-ended genomic fragments. An adenine residue was added by terminal transferase to the 3' end, and the resulting fragments were ligated to Solexa adapters. The products were separated by agarose gel electrophoresis, and the band between 150 and 200 bp was excised from the gel. The DNA fragments were extracted from the agarose slice using a QIAquick Gel Extraction Kit (Qiagen). Adapter-modified DNA fragments were enriched by an 18-cycle PCR using Solexa universal adapter primers. The DNA fragment library was quantitated, and then diluted to a 10-nM working stock for cluster generation. Adapter-ligated fragments (2 nM) were denatured in 0.1 M NaOH for 5 min, then further diluted to a final 9 pM concentration in 1 mL of prechilled hybridization buffer, and introduced onto the Solexa flow cell using the Cluster Station. Following isothermal amplification, clusters were made single-stranded by 0.1 M NaOH denaturation, metered across the flow cell by the Solexa Cluster Station. A sequencing primer complementary to one Solexa adapter was added to prime the single strands of each cluster. Once hybridized and with excess primer removed by a wash, the flow cell was ready for sequencing. The Solexa Genome Analyzer II was programmed to provide up to 36 sequential flows of fluorescently labeled, 3'-OH blocked nucleotides and polymerase to the surface of the flow cell, thus producing a fixed 36-bp read length. After each base incorporation step, the flow cell surface was washed to remove reactants and then imaged by microscope objective. The experiments collected 300 tiled images ("tiles") per flow cell lane, each containing on average 30,000 clusters.

SNP Analysis

The two lanes' sequencing results were mapped onto the reference genome L. reuteri JCM 1112T (GenBank accession no AP007281) separately. The mapping software Maq version 0.6.6 (http://maq.sourceforge.net/maq-man.shtml) was used to perform the mapping (default parameters). SNPs were identified and validated by the MAQ software, and classified into coding SNP and intergenetic SNPs. Coding SNPs were identified as synonymous and nonsynonymous. The SNPs were finally verified by PCR amplification of the surrounding region, followed by Sanger sequence determination.

Example 4

Method of Selection of Strains

The selection of strains effective for prevention of bone loss is based on the ability to restore altered microbial communities. Based on the results of examples 1 and 2, L. reuteri ATCC PTA 6475 is selected based on the fact that this strain has the ability to restore altered microbial communities. L. reuteri ATCC PTA 4659 is not selected based on the results of example 2.

Example 5

Method of Selection of Strains

The selection of strains effective for prevention of bone loss is based on the presence of certain SNPs. As a consequence of the results of example 3, L. reuteri ATCC PTA 6475 is selected, since it harbors all of the four sought SNPs. Due to the lack of these SNPs L. reuteri ATCC PTA 4659 is not selected.

Example 6

Method of Selection of Strains

The selection of strains effective for prevention of bone loss is based on example 3 and 4 and 5, strains harboring at least one of the four sought SNPS as well as the capacity to restore altered microbial communities is selected. Based on these criteria L. reuteri ATCC PTA 6475 is selected.

Example 7

L. reuteri ATCC PTA 6475 Suppresses Ovx Induced Bone Loss

In this study ovariectomized (ovx) BALB/c mice were used as a mouse model for bone loss. Mice (12 weeks old) were ovariectomized and divided into two groups were the first group was treated with L. reuteri ATCC PTA 6475 three times a week during four weeks. BALB/c that had not been ovariectomized were used as a control group. Distal femur bone volume fraction (BV/TV) and bone TRAP5 RNA (relative to HPRT) were measured. Mice treated with L. reuteri ATCC PTA 6475 showed the same bone volume fraction as the control group. Further it was to be seen that TRAP5 (a marker of osteoclast function) is returned to baseline (control group) upon L. reuteri ATCC PTA 6475 treatment.

Figure 2:
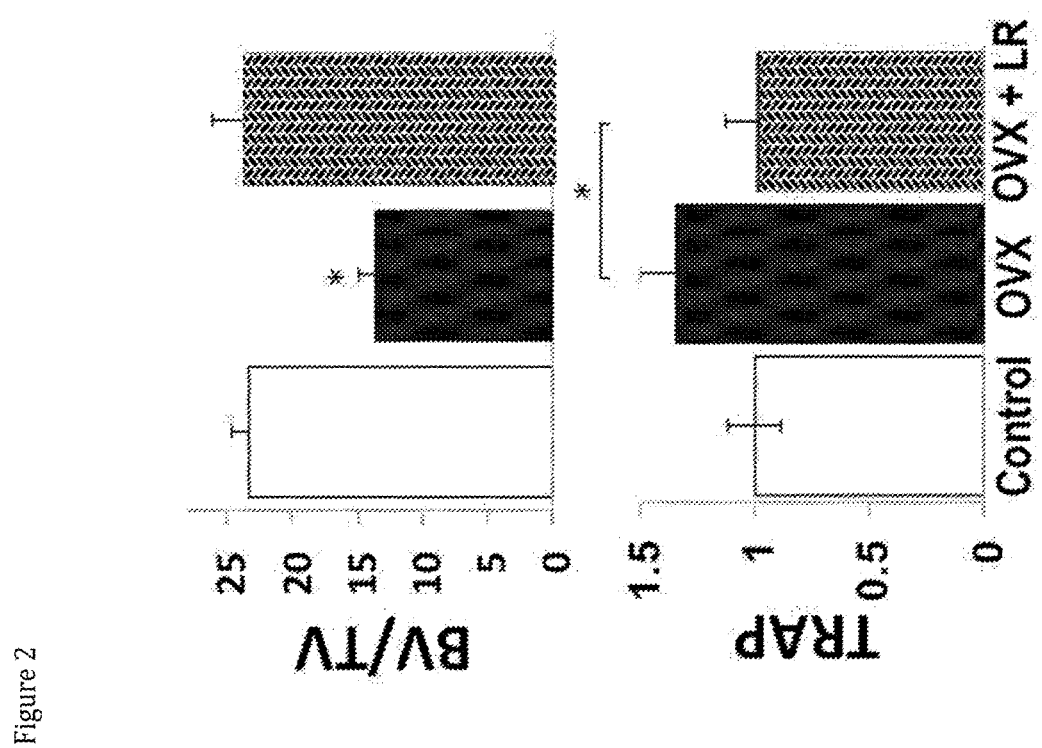
FIG. 2 shows the suppression of bone loss by L. reuteri ATCC PTA 6475.

FIG. 2 shows that the suppression of bone loss by L. reuteri ATCC PTA 6475 is nearly 100% and that the expression of TRAP5 is returned to baseline.

Example 8

The Selected L. reuteri ATCC PTA 6475 is Superior to the Non-Selected L. reuteri ATCC PTA 4659 in Suppressing Bone Loss.

Figure 3:
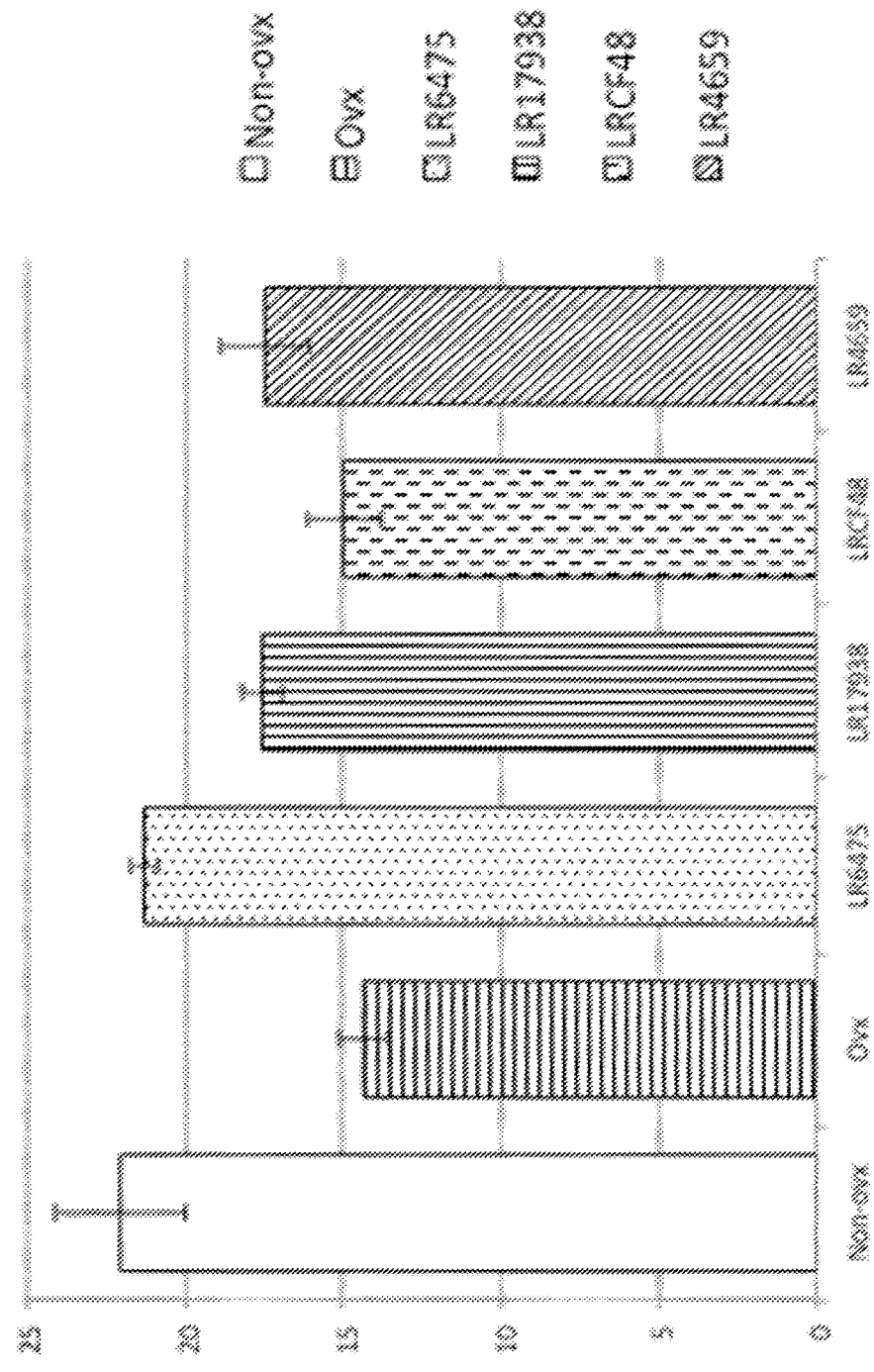
FIG. 3 shows the effect on bone loss in different L. reuteri strains.

In this experiment we gavaged animals three times per week with the L. reuteri ATCC PTA 6475 and L. reuteri ATCC PTA 4659 strains while also providing the strains continuously in the drinking water for 28 days. Distal femur bone volume fraction (BV/TV) was measured by μCT. L. reuteri ATCC PTA 6475 suppressed bone loss and was indistinguishable from control mice (FIG. 3). L. reuteri ATCC PTA 4659 did not suppress bone loss to a sufficient level that reached statistical significance (p<0.01). L. reuteri ATCC PTA 4659 is not as effective as the selected strain L. reuteri ATCC PTA 6475.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09968643B2). An electronic copy of the "Sequence Listing" will also be available from the USPTO upon request and payment of the fee set forth in 37 CFR 1.19(b)(3).

The invention claimed is:

1. A method for the treatment or prevention of bone loss, comprising administering to an individual in need thereof a lactic acid bacterial strain comprising a nucleic acid sequence having at least 95% identity to the nucleic acid sequence of the genome of *L. reuteri* JCM 1112 (SEQ ID NO: 1), and harboring an identical nucleotide relative to the genome of *L. reuteri* JCM 1112 (SEQ ID NO: 1) in at least one of the following four positions: C in base pair 271 391, G in base pair 453 538, G in base pair 529 228, and C in base pair 599 338, wherein the lactic acid bacterial strain is *L. reuteri* ATCC PTA 6475.

* * * * *